US00PP23985P3

(12) United States Plant Patent
Beatson

(10) Patent No.: US PP23,985 P3
(45) Date of Patent: Oct. 15, 2013

(54) HOP PLANT NAMED 'HORT3829'

(50) Latin Name: ***Humulus lupulus* L.**
Varietal Denomination: Hort3829

(75) Inventor: Ron Beatson, Motueka (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 13/135,412

(22) Filed: Jul. 5, 2011

(65) Prior Publication Data

US 2013/0014300 P1 Jan. 10, 2013

(51) Int. Cl.
*A01H 5/00* (2006.01)

(52) U.S. Cl.
USPC ..... Plt./236

(58) Field of Classification Search
USPC ..... Plt./236
See application file for complete search history.

*Primary Examiner* — Kent L Bell
(74) *Attorney, Agent, or Firm* — Lathrop & Gage LLP

(57) ABSTRACT

A new and distinct Hop plant is described. The triploid cultivar results out of selection from a population of seedlings derived from the open pollination of the cultivar 'Hallertauer Mittelfrueh' (not patented). The cones are of a medium size, oval shape and ripen early. The new cultivar produces cones suitable for beer flavouring in the aroma hops market.

4 Drawing Sheets

Genus and species of plant claimed: *Humulus lupulus* L.
Variety denomination: 'Hort3829'.

BACKGROUND TO THE INVENTION

The new cultivar was selected from a population of triploid seedlings derived from the open pollination of 'Hallertauer Mittelfrueh' (tetraploid version) in the 1998/99 season. Triploid seedlings obtained from this cross were grown in a nursery at Motueka, New Zealand in the 1999/2000 season. The resulting seedlings were then planted out in the field and grown in the 2000/01 season, during this season 'Hort3829' was selected and given the breeder code of 99-38-29. This cultivar was selected on the basis of its agronomic performance, seedlessness and chemistry profile.

SUMMARY OF THE INVENTION

A new and distinct Hop plant is described. The cones of 'Hort3829' are of a medium size, oval shape and ripen early. The new cultivar produces cones suitable for beer flavouring in the aroma hops market.

'Hort3829' was relocated to the seedling selections repository, at the Motueka site, in 2001/02 where it underwent performance monitoring for agronomic and chemistry traits of commercial importance during 2001/02 and 2002/03. In 2001/02 it was asexually propagated via rhizome cuttings in anticipation of good performance for a small plot replicated trial. For three seasons, from 2002/03 to 2004/05, 'Hort3829' was trialed, along with ten other promising aroma selections and a control of 'Pacifica' (not patented), for its commercial potential. In the winter of 2005 it was decided to advance 'Hort3829' to large-scale testing. Over the next five seasons the cultivar underwent extensive brewing, agronomic, and chemistry evaluations in 150-plant plots at Motueka, New Zealand. In addition, two 500-plant grower trials were conducted in the Motueka area during the 2005-06 to 2010-11 seasons.

'Hort3829' is maintained at Motueka as a 150-plant plot where it has undergone observations for uniformity. All plants have been found to be true to type, that is, no off types have been observed. Under New Zealand growing conditions 'Hort3829' is distinguished from the known parental cultivar 'Hallertauer Mittelfrueh' and other varieties of common knowledge by the following characteristics along with its unique chemistry profile and brewing characteristics.

'Hallertauer Mittelfrueh': early season shoots of 'Hort3829' are reddish-green while those of 'Hallertauer Mittelfrueh' are green.

'New Zealand Hallertauer': when mature 'Hort3829' vines have an overall fusiform to cylindrical with a medium head volume, while 'New Zealand Hallertauer' is cylindrical in shape with a low head volume, longer laterals and on average a higher yield.

'Pacifica': when mature 'Hort3829' vines have an overall fusiform to cylindrical with a red stripe, while 'Pacifica' is cylindrical in shape with a green stripe.

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustrations of this character.

DETAILED DESCRIPTION

The following is a description of the new cultivar with colour terminology in accordance with The Royal Horticultural Society Colour Charts (R.H.S.C.C.) 2001 edition. The specimens described were grown at Motueka, New Zealand. The observations were made over the 2009-2011 seasons.

Plant form and vigour: Plants are a normal growth type and are fusiform to cylindrical in shape and they produce a moderate yield (1500-2200 kg/ha) of early maturing cones. The main shoot has a medium anthocyanin colouration with a near greyed purple 187B stripe, background colour of near green 143B with near red purple 59B flecks and few thorns. One-year-old single strung plants near to harvest maturity had an average main shoot diameter of 10.8 mm with an average internode length of 203 mm.

Laterals: The side shoots from the middle third of the plant are short in length (an average of approximately 400 mm) and produce a medium number of cones, approximately 12 per node, with an average of 8 nodes per lateral. The upper third of the plant also produces short laterals (an average of 420 mm) and a medium number of cones, approximately 13 per node, with an average of 8 nodes per lateral; the laterals are evenly distributed along the length of the plant. The density of foliage on the laterals is considered to be moderately dense.

Figure 2:
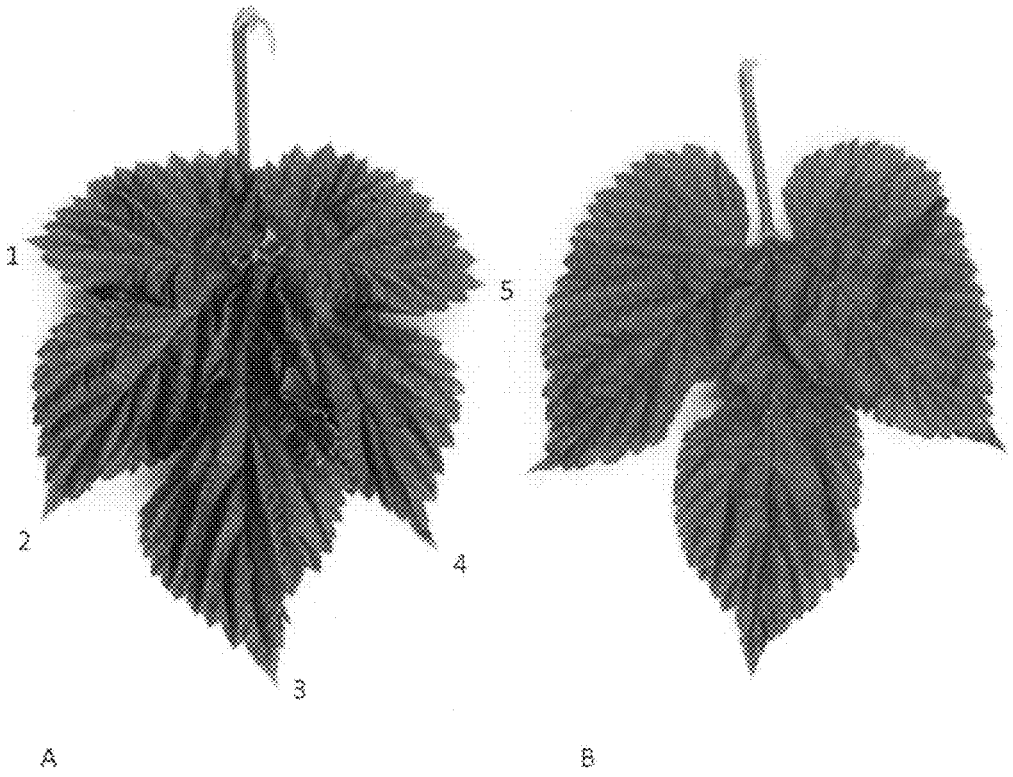
FIG. 2: Mature fully expanded leaves of 'Hort3829' (A) and 'New Zealand Hallertauer' (B).
Figure 3:
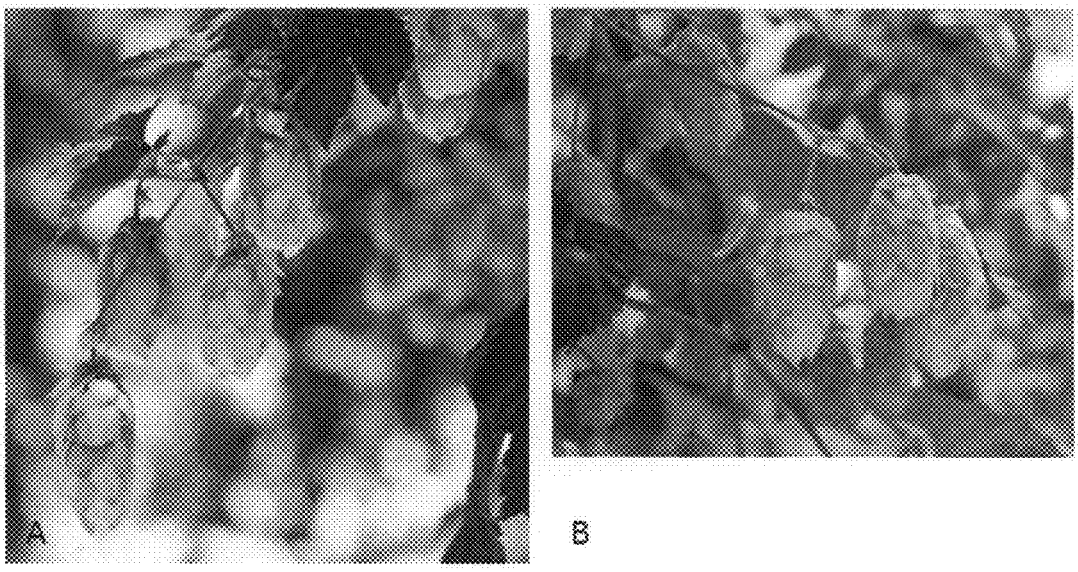
FIG. 3: Cones of 'Hort3829' (A) and 'New Zealand Hallertauer' (B).
Figure 4:
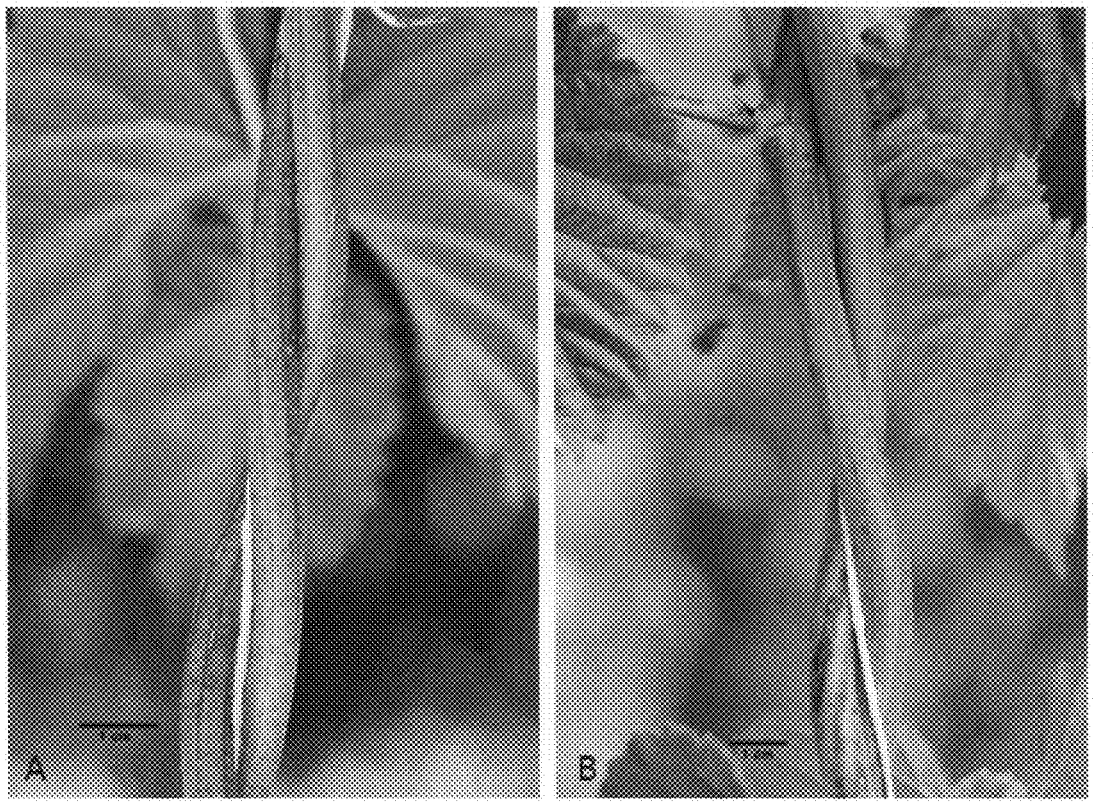
FIG. 4: Close up of mature vines 'Hort3829' (A) and 'New Zealand Hallertauer' (B).

Leaves: Typical leaf arrangement was opposite. The lamina shape is palmatifid with between three and five strong lobes with a dentate margin and acuminate apices, the basal lobes typically imbricate, the upper surface has a very weak gloss, as opposed to the 'Pacifica' lamina which has three lobes and a medium gloss on the upper surface. The length of the lobes averaged 75.2 mm for the two shorter lobes, numbered 1 and 5 (see FIG. 2) and 122.5 mm for the three longer lobes, numbered 2, 3, and 4. Lobes were measured from the tip to where they joined. The colour of the upper side of the leaves was near green 139A while the lower side was between near green 137C and 138A. The colour of the veins was near yellow-green 146C and 146D, this colouration extended down the length of the underside of the petiole. The remainder of the petioles were coloured near greyed-orange 166A. The petiole had an average length of 90.9 mm and an average width of 4.8 mm. The petioles and both the topside and underside of leaves had a different trichome form on them. The topside of the leaves had white strigose trichomes, the underside near yellow-green 145B strigose trichomes, while the petiole and underside main vein had raised lumps the same colour as the surrounding tissue topped with bifid transparent trichomes.

Stipules: Were connate medium sized, upright, with an acute apex which typically splits, and green in colour.

Cones: Are medium sized, an average of 46.5 mm long and 24.2 mm in diameter at the widest point, compact, oval in shape, and near yellow green 144B and 144C in colour. The closed bracts were an average of 19.8 mm long and 12.4 mm wide at the widest point, with a medium length apex and an acute tip. Cones are early maturing between 1st and 10th March under average New Zealand conditions.

Figure 1:
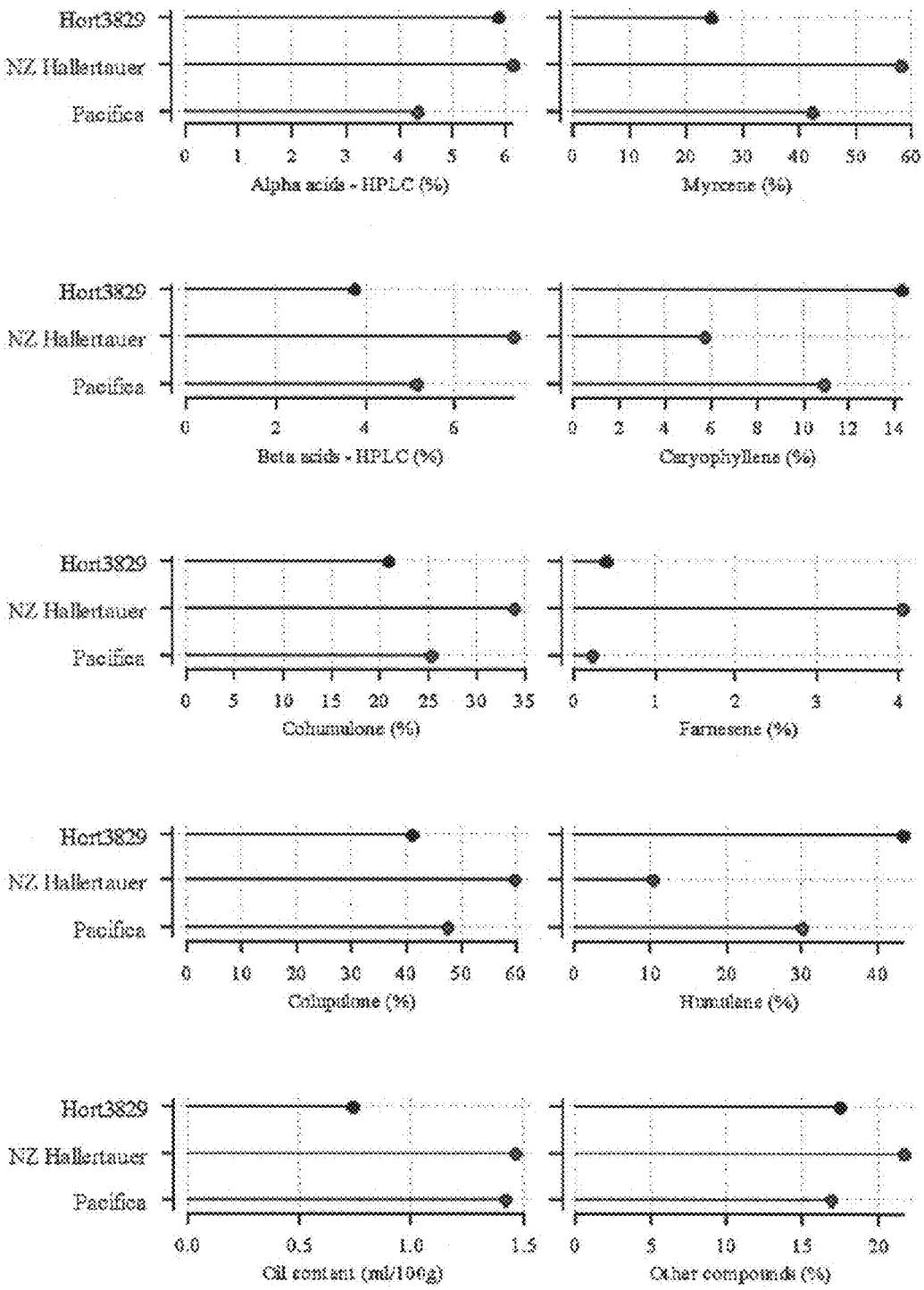
FIG. 1: Five year mean of chemistry profiles for 'Hort3829' at harvest and two comparator cultivars 'New Zealand Hallertauer' (not patented) and 'Pacifica' (not patented). Trials and testing was conducted in Motueka, New Zealand.

Chemistry profile: 'Hort3829' has undergone extensive chemistry profile testing and the following are the averages of five years of data (FIG. 1). The data provided compares 'Hort3829' with 'Pacifica' and 'New Zealand Hallertauer' as these are commonly grown aroma hop cultivars in New Zealand. The chemistry profile of 'Hort3829' differs significantly from both 'Pacifica' and 'New Zealand Hallertauer' in a number of ways; these include a higher percentage of alpha acids than 'Pacifica' and a lower percentage of beta acids than either of the comparators. The cohumulone percentage is also consistently lower, with an average of 21, 25, and 34 percent for 'Hort3829', 'Pacifica', and 'New Zealand Hallertauer' respectively. The proportion of essential oils at harvest found in 'Hort3829' cones differs considerably from that found in either 'Pacifica' or 'New Zealand Hallertauer' as does the overall oil content (mg/100 g). Consequently 'Hort3829' delivers a unique flavour, aroma, and bittering quality when processed and is therefore considered to be distinct. 'Hort3829' has no known particular tolerances or susceptibilities to pests and diseases associated with hop plants.

Use: Flavouring and bittering ingredient for beer in the aroma market.

The invention claimed is:

1. A new and distinct Hop plant substantially as herein illustrated and described.

* * * * *